(12) United States Patent
Suzuki et al.

(10) Patent No.: US 8,440,717 B2
(45) Date of Patent: May 14, 2013

(54) HAIR GROWTH REGULATING AGENT

(75) Inventors: Yasuto Suzuki, Haga-gun (JP); Naoko Morisaki, Sumida-ku (JP); Michiyo Sasajima, Haga-gun (JP)

(73) Assignee: Kao Corporation, Tokyo (JP)

( * ) Notice: Subject to any disclaimer, the term of this patent is extended or adjusted under 35 U.S.C. 154(b) by 162 days.

(21) Appl. No.: 13/056,389

(22) PCT Filed: Aug. 4, 2009

(86) PCT No.: PCT/JP2009/064099
§ 371 (c)(1),
(2), (4) Date: Jan. 28, 2011

(87) PCT Pub. No.: WO2010/016606
PCT Pub. Date: Feb. 11, 2010

(65) Prior Publication Data
US 2011/0130456 A1  Jun. 2, 2011

(30) Foreign Application Priority Data
Aug. 5, 2008 (JP) .................... 2008-202234

(51) Int. Cl.
*A61K 8/41* (2006.01)
(52) U.S. Cl.
USPC ........................................... 514/547
(58) Field of Classification Search ........... None
See application file for complete search history.

(56) References Cited

U.S. PATENT DOCUMENTS

| 5,939,458 A | 8/1999 | Henry et al. |
| 2003/0199584 A1 | 10/2003 | Ahluwalia et al. |
| 2005/0003024 A1 | 1/2005 | Oblong et al. |
| 2008/0059313 A1 | 3/2008 | Oblong et al. |

FOREIGN PATENT DOCUMENTS

| DE | 198 26 529 A1 | 12/1999 |
| WO | WO 88/08295 A1 | 11/1988 |
| WO | WO 99/15136 A1 | 4/1999 |
| WO | WO 03/086331 | 10/2003 |
| WO | WO 2008/027541 A2 | 3/2008 |

OTHER PUBLICATIONS

International Search Report for PCT/JP2009/064099; I.A. fd: Aug. 4, 2009, mailed Jan. 29, 2010 from the European Patent Office, Rijswijk, The Netherlands.

International Preliminary Report on Patentability, Chapter I of the Patent Cooperation Treaty, including the Written Opinion for PCT/JP2009/064099; I.A. fd: Aug. 4, 2009, issued Feb. 8, 2011 from the International Bureau of WIPO, Geneva, Switzerland.

*Primary Examiner* — Blessing Fubara
*Assistant Examiner* — Jennifer Berrios
(74) *Attorney, Agent, or Firm* — Sterne, Kessler, Goldstein & Fox P.L.L.C.

(57) ABSTRACT

A method for regulating hair growth is provided which comprises administering, to a subject in need thereof, dodecylcarbomoylmethyltrimethylammonium chloride and/or a compound of salt thereof selected from 2-dimethylamino-N-ethyl-acetamide, 2-dimethylamino-N-(2-{2-[2-(2-dimethylamino-acetylamino)-ethoxy]-ethoxy}-ethyl)-acetamide, 2-dimethylamino-N-[8-(2-dimethylamino-acetylamino)-octyl]-acetamide, 2-dimethylamino-N-[2-(2-{2-[2-(2-dimethylamino-acetylamino)-ethoxy]-ethoxy}-ethoxy)-ethyl]-acetamide, 2-dimethylamino-N-[12-(2-dimethylamino-acetylamino)-dodecyl]-acetamide, and 2-dimethylamino-N-[4-(2-dimethylamino-acetamino)-butyl]acetamide.

9 Claims, No Drawings

HAIR GROWTH REGULATING AGENT

TECHNICAL FIELD OF THE INVENTION

The present invention relates to a hair growth regulating agent.

BACKGROUND OF THE INVENTION

From the viewpoint of biology, head hair and body hair are tissues that protect important organs and body parts, such as the head, breast, and limbs. However, in recent years, there has been an increasing tendency that little body hair on particular body parts (e.g., limbs) is considered favorable from the viewpoint of aesthetic appearance.

Removal of body hair is performed through, for example, a mechanical removal method using a shaver, a hair remover, or the like, or a chemical removal method using an epilation or depilation agent. However, such body hair removal methods may involve physical or chemical stimulation of the skin, and is not yet satisfactory in terms of hair growth regulating effect. In addition, the methods require a retreatment for body hair removal after the elapse of a certain period of time. Thus, demand has arisen for reducing the frequency of body hair removal treatments.

Patent Document 1 discloses a method of reducing hair growth including topical application of a composition containing α-difluoromethylornithine and a penetration enhancer. However, Patent Document 1 does not describe data showing that the composition actually reduces hair growth.

Patent Document 1: WO 03/086331 pamphlet

SUMMARY OF THE INVENTION

The present invention provides a hair growth regulating agent containing, as an active ingredient, a compound represented by the following formula (I):

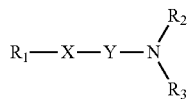

[wherein $R_1$ represents a substituted or unsubstituted, linear or branched C2 to C25 alkyl group; a group represented by the following formula (II):

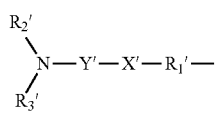

(wherein $R_1'$ represents a substituted or unsubstituted, linear or branched C2 to C20 alkylene group, or —$(CH_2)_n$-{O—$(CH_2)_m$}$_o$—O—$(CH_2)_p$— in which each of n, m, o, and p is an integer from 1 to 6; X' represents —CO—NH—, —O—CO—O—, —NH—CO—, —CO—O—, —O—CO—, or —O—; Y' represents a substituted or unsubstituted C1 to C4 alkylene group; $R_2'$ represents a hydrogen atom or a C1 to C4 alkyl group; $R_3'$ represents a C1 to C4 alkyl group; and when $R_2'$ and $R_3'$ each represent a C1 to C4 alkyl group, the two alkyl groups may be identical to or different from each other); or a group represented by the following formula (III):

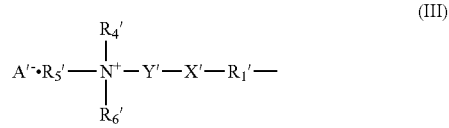

(wherein $R_1'$, X', and Y' have the same meanings as defined above; $R_4'$, $R_5'$, and $R_6'$, which may be identical to or different from one another, each represent a C1 to C4 alkyl group; and $A'^-$ represents a counter ion);

X represents —CO—NH—, —O—CO—O—, —NH—CO—, —CO—O—, —O—CO—, or —O—;

Y represents a substituted or unsubstituted C1 to C4 alkylene group;

$R_2$ represents a hydrogen atom or a C1 to C4 alkyl group;

$R_3$ represents a C1 to C4 alkyl group; and when $R_2$ and $R_3$ each represent a C1 to C4 alkyl group, the two alkyl groups may be identical to or different from each other] or a salt of the compound; and/or a quaternary ammonium salt represented by the following formula (IV):

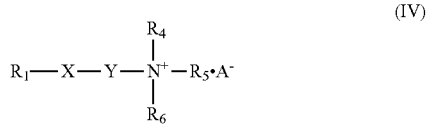

(wherein $R_1$, X, and Y have the same meanings as defined above; $R_4$, $R_5$, and $R_6$, which may be identical to or different from one another, each represent a C1 to C4 alkyl group; and $A^-$ represents a counter ion).

The present invention also provides a cosmetic composition for depilation and/or epilation comprising the hair growth regulating agent.

The present invention also provides a method for regulating hair growth, comprising administering the aforementioned compound or a salt thereof and/or the aforementioned quaternary ammonium salt to a subject in need thereof.

The present invention also provides use of the aforementioned compound or a salt thereof and/or the aforementioned quaternary ammonium salt for producing a hair growth regulating agent.

The present invention also provides use of the aforementioned hair growth regulating agent for producing a cosmetic composition for depilation and/or epilation.

PREFERRED EMBODIMENT FOR CARRYING OUT THE INVENTION

The present inventors have conducted extensive studies, and as a result have found that compounds represented by the aforementioned formulas exhibit hair growth regulating activity. The present invention provides a hair growth regulating agent containing a compound represented by the aforementioned formulas as an active ingredient. According to the present invention, there is provided a hair growth regulating agent exhibiting satisfactory hair growth regulating effect.

The present invention will next be described in detail.

The hair growth regulating agent of the present invention contains a compound represented by formula (I) or a salt thereof, and/or a quaternary ammonium salt represented by formula (IV). The hair growth regulating agent of the present invention exhibits an effect of regulating growth of hair, such as body hair (e.g., unwanted hair). As used herein, the expression "hair growth regulating effect" refers to both a hair growth suppressing effect and an epilation facilitating effect. Particularly, the hair growth regulating agent of the present invention can act on hair (e.g., hair follicles) in the anagen phase (e.g., one-month-old hair to five-year-old hair) and inhibit the growth thereof, to thereby suppress hair growth.

The linear or branched C2 to C25 alkyl group represented by $R_1$ in formula (I) or (IV) is a linear or branched alkyl group having 2 to 25 carbon atoms. Examples of the linear or branched C2 to C25 alkyl group include ethyl, n-propyl, i-propyl, n-butyl, i-butyl, sec-butyl, t-butyl, n-pentyl, n-hexyl, 2-ethylhexyl, n-heptyl, n-octyl, n-nonanyl, n-decyl, trimethyldecyl, n-undecyl, n-dodecyl, n-tridecyl, n-tetradecyl, n-pentadecyl, n-hexadecyl, n-heptadecyl, n-octadecyl, methylheptadecyl (methyl-branched isostearyl), n-nonadecyl, n-icosyl, n-henicosanyl, n-docosanyl, n-tricosanyl, n-tetracosanyl, and n-pentacosanyl. Preferred are linear or branched C6 to C20 alkyl groups, such as n-hexyl, 2-ethylhexyl, n-heptyl, n-octyl, n-nonanyl, n-decyl, trimethyldecyl, n-undecyl, n-dodecyl, n-tridecyl, n-tetradecyl, n-pentadecyl, n-hexadecyl, n-heptadecyl, n-octadecyl, methylheptadecyl (methyl-branched isostearyl), n-nonadecyl, and n-icosyl.

Alternatively, $R_1$ in formula (I) or (IV) is a group represented by formula (II) or (III).

The linear or branched C2 to C20 alkylene group represented by $R_1'$ in formula (II) or (III) is a linear or branched alkylene group having 2 to 20 carbon atoms. Examples of the linear or branched C2 to C20 alkylene group include ethylene, trimethylene, tetramethylene, pentamethylene, hexamethylene, heptamethylene, octamethylene, nonamethylene, decamethylene, undecamethylene, dodecamethylene, tridecamethylene, tetradecamethylene, pentadecamethylene, hexadecamethylene, heptadecamethylene, octadecamethylene, nonadecamethylene, icosadecamethylene, methylethylene, ethylethylene, propylene, and propenylene. Preferred are linear or branched C2 to C16 alkylene groups, such as ethylene, trimethylene, tetramethylene, pentamethylene, hexamethylene, heptamethylene, octamethylene, nonamethylene, decamethylene, undecamethylene, dodecamethylene, tridecamethylene, tetradecamethylene, pentadecamethylene, hexadecamethylene, methylethylene, ethylethylene, and propylene. Alternatively, $R_1'$ in formula (II) or (III) is —$(CH_2)_n$—{O—$(CH_2)_m$}$_o$—O—$(CH_2)_p$— in which each of n, m, o, and p is an integer from 1 to 6, preferably, each of n, m, and p is 2, and o is 1.

In formula (II) or (III), X' represents —CO—NH—, —O—CO—O—, —NH—CO—, —CO—O—, —O—CO—, or —O—, and is preferably —CO—NH—.

The C1 to C4 alkylene group represented by Y' in formula (II) or (III) includes a methylene group, an ethylene group, a propylene group, and a butylene group, and preferably a methylene group.

In formula (II), $R_2'$ represents a hydrogen atom or a C1 to C4 alkyl group, and $R_3'$ represents a C1 to C4 alkyl group. In formula (III), each of $R_4'$, $R_5'$, and $R_6'$ represents a C1 to C4 alkyl group. Examples of the C1 to C4 alkyl group include methyl, ethyl, propyl, and butyl. When $R_2'$ and $R_3'$ each represent a C1 to C4 alkyl group, the two alkyl groups may be identical to or different from each other, and $R_4'$, $R_5'$, and $R_6'$ may be identical to or different from one another.

Examples of the counter ion represented by $A'^-$ in formula (III) include a halogen ion, a carboxylate ion, a sulfonate ion, a sulfate ion, and a nitrate ion. Preferred are a halogen ion and a carboxylate ion. Examples of the halogen ion include fluorine ion, chlorine ion, bromine ion, and iodine ion. Examples of the carboxylate ion include formate ion, acetate ion, propionate ion, fumarate ion, and malate ion.

In formula (I) or (IV), X represents —CO—NH—, —O—CO—O—, —NH—CO—, —CO—O—, —O—CO—, or —O—. When $R_1$ is a linear or branched C2 to C25 alkyl group, X is preferably —CO—NH— or —NH—CO—, whereas when $R_1$ is a group represented by formula (II) or (III), X is preferably —NH—CO—.

Examples of the C1 to C4 alkylene group represented by Y in formula (I) or (IV) include methylene, ethylene, propylene, and butylene. When $R_1$ is a linear or branched C2 to C25 alkyl group, Y is preferably a methylene group or an ethylene group, whereas when $R_1$ is a group represented by formula (II) or (III), Y is preferably a methylene group.

In formula (I), $R_2$ represents a hydrogen atom or a C1 to C4 alkyl group, and $R_3$ represents a C1 to C4 alkyl group. In formula (IV), each of $R_4$, $R_5$, and $R_6$ represents a C1 to C4 alkyl group. Examples of the C1 to C4 alkyl group include methyl, ethyl, propyl, and butyl. When $R_2$ and $R_3$ each represent a C1 to C4 alkyl group, the two alkyl groups may be identical to or different from each other, and $R_4$, $R_5$, and $R_6$ may be identical to or different from one another.

The counter ion represented by $A^-$ in formula (IV) includes the same as those of the aforementioned counter ion $A'^-$.

The C2 to C25 alkyl group represented by $R_1$ in formula (I) or (IV), the C1 to C4 alkylene group represented by Y in formula (I) or (IV), the C2 to C20 alkylene group represented by $R_1'$ in formula (II) or (III), or the C1 to C4 alkylene group represented by Y' in formula (II) or (III) may be substituted with one or more substituents. Examples of such a substituent include a halogen atom, a hydroxyl group, an alkoxyl group, an acyl group, an optionally protected amino group, and a heterocyclic group. Examples of the halogen atom include a chlorine atom, a bromine atom, and an iodine atom. The alkoxyl group is preferably a C1 to C12 alkoxyl group, including a methoxy group, an ethoxy group, and an isopropoxy group. The acyl group is preferably a C1 to C12 alkanoyl group, including a formyl group, an acetyl group, a propionyl group, or a butyryl group. Examples of the optionally protected amino group include an amino group, an acylamino group, an alkylamino group, and a dialkylamino group. The heterocylic group is preferably, for example, a 5- to 14-membered monocyclic or condensed cyclic group containing one to three nitrogen atoms, oxygen atoms, and/or sulfur atoms as hetero atoms, including a pyridyl group, a pyridazinyl group, a furyl group, a thienyl group, an indolyl group, a thiazolyl group, an imidazolyl group, a benzofuryl group, or a benzothienyl group.

Examples of salts of the compound represented by formula (I) (excluding the case where $R_1$ is a group represented by formula (III)) include inorganic acid salts such as hydrochloride, sulfate, phosphate, hydrobromide, hydroiodide, nitrate, pyrosulfate, and metaphosphate; organic acid salts such as citrate, benzoate, acetate, propionate, fumarate, maleate, and sulfonate (e.g., methanesulfonate, p-toluenesulfonate, or naphthalenesulfonate); and amino acid salts such as glutamate and aspartate.

Preferred examples of the compound represented by formula (I) or a salt thereof or the quaternary ammonium salt represented by formula (IV) includes 2-dimethylamino-ethyl dodecanoate, 2-dimethylamino-N-dodecyl-acetamide, dodecyl dimethylaminoacetate, (2-dodecyloxy-ethyl)-dimethylamine, dodecanoic acid (2-dimethylaminoethyl)-amide, 2-dimethylamino-N-ethyl-acetamide, dodecylcarbamoylmethyltrimethylammonium chloride, bis-(2-dimethylamino-ethyl)pentanedioate dihydrochloride, 2-dimethylamino-N-(2-{2-[2-(2-dimethylamino-acetylamino)-ethoxy]-ethoxy}-ethyl)-acetamide, 2-dimethylamino-N-[8-(2-dimethylamino-acetylamino)-octyl]-acetamide, 2-dimethylamino-N-[2-(2-{2-[2-(2-dimethylamino-acetylamino)-ethoxy]-ethoxy}-ethoxy)-ethyl]-acetamide, 2-dimethylamino-N-[12-(2-dimethylamino-acetylamino)-dodecyl]-acetamide, and 2-dimethylamino-N-[4-(2-dimethylamino-acetamino)-butyl]-acetamide.

The compound represented by formula (I) or the salt thereof, or the quaternary ammonium salt represented by formula (IV) may be produced through, for example, the method described in Izv. Vyssh. Ucheb. Zaved., Khim. Khim. Tekhnol., 14 (9), 1369 (1971); for example, by reacting choline chloride with a fatty acid chloride under a stream of nitrogen.

A hair growth regulating composition may be produced through a customary method by appropriately mixing the hair growth regulating agent of the present invention with, in consideration of the intended use of the composition, any component generally used in cosmetic compositions, quasi drugs, drugs, or the like (e.g., a humectant, powder, a gelation agent, a thickener, a surfactant, an emulsifier, an anti-inflammatory agent, an antioxidant, a pH-adjusting agent, a chelating agent, a preservative, a dye, or a perfume), or a component exhibiting a hair growth controlling effect or an epilation effect (e.g., a keratolytic agent, or thioglycolic acid or a salt thereof). Examples of the keratolytic agent include lactic acid, Bioplase, salicylic acid, glycolic acid, citric acid, malic acid, sulfur, resorcin, thioxolone, selenium disulfide, and urea. Examples of the thioglycolic acid salt include a sodium salt, a potassium salt, a calcium salt, an ammonium salt, and salts of alkanolamines such as monoethanolamine, diethanolamine, and triethanolamine. Preferred is calcium thioglycolate.

The hair growth regulating agent of the present invention may be incorporated into a pharmaceutical agent for skin external use or a cosmetic composition. No particular limitation is imposed on the pharmaceutical agent for skin external use, and examples thereof include external-use agents for application, spraying, plastering, etc., such as lotion, emulsion, suspension, cream, ointment, stick, sheet, and patch. No particular limitation is imposed on the cosmetic composition, but the composition is preferably a cosmetic composition relating to depilation, epilation or shaving. Specific examples of such a cosmetic composition include depilation agents in the form of, for example, paste, cream, or aerosol; epilation agents in the form of, for example, wax, gel, or sheet; post-treatment compositions (e.g., lotion and cream) used for treatment after depilation or epilation; antiperspirant or deodorant cosmetic compositions (e.g., deodorant lotion, deodorant powder, deodorant spray, and deodorant stick); pre-shave compositions (e.g., pre-shave lotion); shaving compositions (e.g., shaving cream); and after-shave compositions (e.g., after-shave lotion).

The compound represented by formula (I) and/or the quaternary ammonium salt represented by formula (IV) is incorporated into the hair growth regulating agent of the present invention in an amount of, for example, 0.0001 to 20 wt.%, preferably 0.001 to 5 wt.%.

The amount of the hair growth regulating agent of the present invention to be applied to a subject in need thereof may depend on the density or amount, or other conditions of body hair of the subject. For example, the hair growth regulating agent of the present invention may be applied once or several times a day, at the amount of 0.001 to 1,200 mg, preferably 0.01 to 300 mg, as the weight of the compound represented by formula (I) and/or the quaternary ammonium salt represented by formula (IV)

As described above, the agent of the present invention inhibits the growth of hair, thereby exhibiting excellent hair growth suppressing effect, with high safety to the human body. Particularly, the effect of the agent of the present invention is prominent for hair in the anagen phase, between one-month to five-years.

EXAMPLES

The present invention will next be described in more detail by way of examples.

Example 1

Synthesis of Compounds of the Present Invention

In the following formulas (V) to (XVII), "-Me" represents a methyl group.
1) Synthesis of 2-Dimethylamino-Ethyl Dodecanoate (Hereinafter May be Referred to as "Compound 1")
Compound 1 represented by the following formula (V):

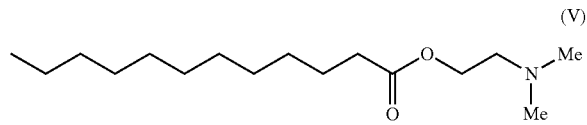 [SMILES: CCCCCCCCCCCC(=O)OCCN(C)C]

was synthesized as follows.

Dimethylaminoethanol (10 g, 11.2 mmol) and chloroform (20 mL) were added to a 50-mL three-necked flask, and the mixture was stirred and cooled to 5° C. in an ice bath. Subsequently, lauroyl chloride (2.5 g, 11.2 mmol) was added dropwise to the mixture over 20 minutes. The resultant mixture was stirred in an ice bath for 0.5 hours and further stirred at room temperature for two hours, and then reaction was completed.

Sodium hydrogencarbonate (1.0 g, 11.8 mmol) and ion-exchange water (10 mL) were added to the resultant reaction mixture, and the mixture was stirred at room temperature for one hour, followed by removal of the aqueous layer. The organic layer was washed with saturated brine (10 mL) and then concentrated under reduced pressure, to thereby yield an oily reaction mixture (1.4 g).

The thus-obtained reaction mixture was subjected to silica gel column chromatography (silica gel 60, 30 g), and elution was carried out with a solvent mixture of chloroform and methanol (chloroform:methanol=100:1 to 1:1), followed by concentration, to thereby yield compound 1 as a colorless, transparent oily product (1.2 g, yield: 78.8%).

The thus-obtained compound 1 was subjected to nuclear magnetic resonance (NMR) spectral analysis and infrared absorption (IR) spectral analysis. The results are shown below.

NMR (MeOH-$d_4$): 0.90 (t, 3H, J=7 Hz), 1.18-1.40 (m, 16H), 1.55-1.70 (m, 2H), 2.28 (s, 6H), 2.32 (t, 2H, J=7 Hz), 2.60 (t, 2H, J=6 Hz), 4.18 (t, 2H, J=6 Hz) ppm $^{13}$C-NMR (MeOH-$d_4$): 14.5, 23.7, 25.9, 30.2, 30.4, 30.5, 30.6, 30.7, 33.1, 34.9, 45.8, 58.6, 62.6, 174.9 ppm IR (NaCl): 3316, 2932, 2810, 2780, 2730, 1742, 1154 cm$^{-1}$ 2) Synthesis of 2-Dimethylamino-N-Dodecyl-Acetamide (Hereinafter May be Referred to as "Compound 2")

Compound 2 represented by the following formula (VI):

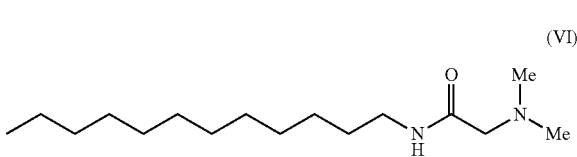 [SMILES: CCCCCCCCCCCCNC(=O)CN(C)C]

(VI)

was synthesized as follows.

N,N-Dimethylglycine methyl ester (1.50 g, 12.8 mmol) was added to n-dodecylamine (1.00 g, 5.4 mmol), and the mixture was stirred at 150 to 160° C. for 5.5 hours. Then, reaction was completed.

After the reaction mixture had been left to cool, ethyl acetate (70 mL) and n-hexane (30 mL) were added to the mixture, and insoluble matter was filtered, followed by concentration, to thereby yield an oily product (1.4 g).

The thus-obtained oily product was subjected to column chromatography, and elution was carried out with a solvent mixture of chloroform and methanol, to thereby yield compound 2 as a pale yellow oily product (1.27 g, yield: 87.0%).

The thus-obtained compound 2 was subjected to NMR spectral analysis and IR spectral analysis. The results are shown below.

NMR (DMSO-$d_6$) δ: 0.84 (t, 3H, J=6 Hz), 1.12-1.40 (m, 20H), 2.17 (s, 6H), 2.80 (s, 2H), 3.04 (q, 2H, J=7 Hz), 7.67 (t, 1H, J=6 Hz) ppm IR (ATR): 2923, 2853, 2777, 1660, 1520 $cm^{-1}$ 3) Synthesis of Dodecyl Dimethylaminoacetate (Hereinafter May be Referred to as "Compound 3")

Compound 3 represented by the following formula (VII):

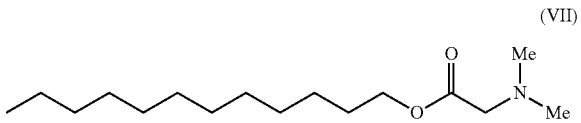 [SMILES: CCCCCCCCCCCCOC(=O)CN(C)C]

(VII)

was synthesized as follows.

N,N-Dimethylglycine methyl ester (1.00 g, 5.6 mmol) and 28% sodium methoxide (0.11 g, 0.6 mmol) were added to n-dodecanol (3.16 g, 17.0 mmol), and the mixture was stirred at 140 to 150° C. for 2.5 hours. Then, reaction was completed.

After the reaction mixture had been left to cool, the mixture was subjected to extraction with ethyl acetate (70 mL), followed by washing with water, and concentration under reduced pressure, to thereby yield an oily product (3.6 g).

The thus-obtained oily product was subjected to column chromatography, and elution was carried out with a solvent mixture of ethyl acetate and n-hexane, to thereby yield compound 3 as a pale yellow oily product (1.18 g, yield: 77.6%).

The thus-obtained compound 3 was subjected to NMR spectral analysis and IR spectral analysis. The results are shown below.

NMR (DMSO-$d_6$) δ: 0.84 (t, 3H, J=7 Hz), 1.13-1.32 (m, 18H), 1.54 (qn, 2H, J=7 Hz), 2.22 (s, 6H), 3.12 (s, 2H), 4.01 (t, 2H, J=7 Hz) ppm IR (ATR): 2924, 2853, 2771, 1736, 1465 $cm^{-1}$ 4) Synthesis of (2-Dodecyloxy-Ethyl)-Dimethylamine (Hereinafter May be Referred to as "Compound 4")

Compound 4 represented by the following formula (VIII):

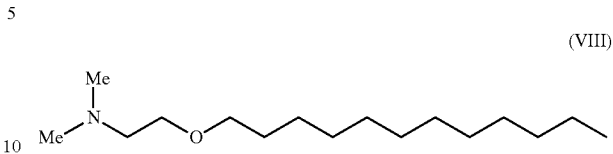

(VIII)

was synthesized as follows.

60% Sodium hydride (0.47 g, 11.2 mmol) was added to a four-necked flask, and dry tetrahydrofuran (50 mL) was added thereto at room temperature under a stream of nitrogen, followed by stirring. To the mixture was added dropwise a solution of dimethylaminoethanol (1.00 g, 11.2 mmol) solved in dry tetrahydrofuran (10 mL) over 20 minutes.

Twenty minutes after dropwise addition, a solution of 1-bromododecane (2.80 g, 11.2 mmol) solved in dry tetrahydrofuran (5 mL) was added dropwise to the resultant mixture over five minutes. After completion of dropwise addition, the resultant mixture was heated to 50° C. and stirred for four hours, and then reaction was completed.

After the reaction mixture had been left to cool, ion-exchange water (20 mL) was added to the mixture, and the mixture was thoroughly stirred. Thereafter, ethyl acetate (100 mL) was added to the mixture for extraction. After washing with water, concentration was carried out under reduced pressure, to thereby yield an oily product (2.68 g).

The thus-obtained oily product was subjected to column chromatography, and elution was carried out with a solvent mixture of chloroform and methanol, to thereby yield compound 4 as a transparent oily product (1.38 g, yield: 47.9%).

The thus-obtained compound 4 was subjected to NMR spectral analysis and IR spectral analysis. The results are shown below.

NMR (CDCl$_3$) δ:0.88 (t, 3H, J=7 Hz), 1.16-1.54 (m, 18H), 1.58 (qn, 2H, J=6 Hz), 2.27 (s, 6H), 2.50 (t, 2H, J=6 Hz), 3.42 (t, 2H, J=7 Hz), 3.51 (t, 2H, J=6 Hz) ppm IR (ATR): 2956, 2915, 2850, 1470, 1120 $cm^{-1}$ 5) Synthesis of Dodecanoic Acid (2-Dimethylaminoethyl)-Amide (Hereinafter May be Referred to as "Compound 5")

Compound 5 represented by the following formula (IX):

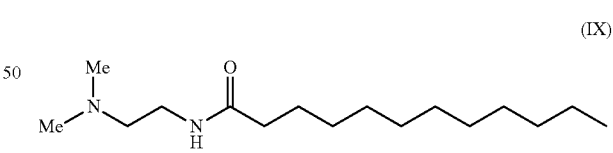

(IX)

was synthesized as follows.

N,N-Dimethylethylenediamine (1.00 g, 11.3 mmol) was dissolved in chloroform (50 mL), and the solution was cooled to 5° C. Subsequently, dodecyl chloride (2.45 g, 11.2 mmol) was added dropwise to the solution over 10 minutes.

After completion of dropwise addition, the resultant mixture was heated to room temperature and stirred for two hours, and then reaction was completed. After completion of reaction, the reaction mixture was concentrated under reduced pressure, and then the residue was subjected to extraction with ethyl acetate (150 mL). After completion of extraction, washing was carried out with saturated aqueous sodium bicarbonate solution (50 mL), and then with saturated brine (50 mL), followed by concentration under reduced pressure, to thereby yield a white solid (2.99 g).

Ion-exchange water (13 mL) was added to the thus-obtained white solid, and the mixture was stirred at 60° C. for 30 minutes. Insoluble matter was filtered, and then the filtrate was cooled to 5° C. After cooling, the resultant crystals were filtered, followed by drying at 40° C. for 12 hours, to thereby yield compound 5 as white crystals (2.45 g, yield: 79.5%).

The thus-obtained compound 5 was subjected to NMR spectral analysis and IR spectral analysis. The results are shown below.

NMR (DMSO-$d_6$) δ: 0.84 (t, 3H, J=7 Hz), 1.12-1.32 (m, 16H), 1.44 (qn, 2H, J=7 Hz), 2.02 (t, 2H, J=7 Hz), 2.12 (s, 6H), 2.23 (t, 2H, J=6 Hz), 3.10 (q, 2H, J=6 Hz), 7.68 (t, 1H, J=7 Hz)

IR (ATR): 2916, 2847, 2820, 1637, 1550 $cm^{-1}$

6) Synthesis of 2-Dimethylamino-N-Ethyl-Acetamide (Hereinafter May be Referred to as "Compound 6")

Compound 6 represented by the following formula (X):

$$\text{(X)}$$

was synthesized as follows.

N,N-Dimethylglycine (0.8 g, 6.8 mmol) was dissolved in 70% aqueous ethylamine solution (5.7 g, 68 mmol), and the solution was sealed in a hermetic container. The solution was stored at 5° C. for three days, and then the solution was concentrated under reduced pressure, to thereby yield an oily product. The oily product was subjected to column chromatography, and elution was carried out with a solvent mixture of chloroform and methanol, to thereby yield compound 6 as a transparent oily product (0.84 g, yield: 94.4%).

The thus-obtained compound 6 was subjected to NMR spectral analysis and IR spectral analysis. The results are shown below.

NMR (DMSO-$d_6$) δ: 0.99 (t, 3H, J=7 Hz), 2.20 (s, 6H), 2.80 (s, 2H), 3.10 (q, 2H, J=7 Hz), 7.73 (br.s, 1H)

IR (ATR): 2973, 2824, 2778, 1651, 1522 $cm^{-1}$

7) Synthesis of Dodecylcarbamoylmethyltrimethylammonium Chloride (Hereinafter May be Referred to as "Compound 7")

Compound 7 represented by the following formula (XI):

$$\text{(XI)}$$

was synthesized as follows.

n-Dodecylamine (60.0 g, 0.32 mol) was dissolved in chloroform (900 mL), and triethylamine (43.2 g, 0.43 mol) was added to the solution, followed by cooling to −50° C. At this temperature, chloroacetyl chloride (40.2 g, 35.6 mol) was added dropwise to the resultant mixture over 30 minutes, and the mixture was further stirred for one hour without intervening the temperature, allowing the reaction to complete.

Ethanol (100 mL) was added to the reaction mixture, and ion-exchange water (300 mL) was further added to the mixture. The mixture was heated to room temperature and then stirred for 20 minutes. After stirring, the mixture was allowed to stand still for phase separation. The thus-obtained lower layer was concentrated, and the residue was subjected to silica gel column chromatography, followed by elution with a solvent mixture of chloroform and methanol. After elution, solvent was removed through evaporation, to thereby yield a residue (85.3 g).

The thus-obtained residue (60.27 g) was added to a stainless steel simple autoclave, and 33% ethanol solution of trimethylamine and ethanol (180 mL) were added thereto, followed by hermetic sealing. The autoclave was heated in an oil bath at 100 to 110° C., and stirring was carried out for five hours. Then, reaction was completed. After cooling to room temperature, pressure was released, and the reaction mixture was concentrated. The resultant residue was subjected to silica gel column chromatography, and elution was carried out with a solvent mixture of chloroform and methanol. After elution, solvent was removed through evaporation, and the residue was recrystallized from a solvent mixture of ethanol and n-hexane, to thereby yield compound 7 as white acicular crystals (55.8 g, yield: 54.3%).

The thus-obtained compound 7 was subjected to NMR spectral analysis. The results are shown below.

NMR (CDCl$_3$) δ: 0.88 (t, 3H, J=7 Hz), 1.25-1.31 (m, 18H), 1.57 (qn, 2H, J=7 Hz), 3.25 (q, 2H, J=6 Hz), 3.49 (s, 9H), 4.70 (s, 2H), 9.22 (t, 1H, J=5 Hz)

8) Synthesis of Bis-(2-Dimethylamino-Ethyl)Pentanedioate Dihydrochloride (Hereinafter May be Referred to as "Compound 8")

Compound 8 represented by the following formula (XII):

$$\text{(XII)}$$

was synthesized as follows.

Dimethylaminoethanol (2.0 g, 22.4 mmol) and chloroform (50 mL) were added to a 100-mL three-necked flask, and the mixture was cooled to 5° C. in an ice bath. Subsequently, diglycolyl chloride (2.0 g, 11.2 mmol) was added dropwise to the flask over five minutes. The resultant mixture was stirred in an ice bath for 0.5 hours, and then precipitation of white solid was observed. Subsequently, stirring was further carried out at room temperature for one hour, and then reaction was completed.

n-Hexane (100 mL) was added to the resultant reaction mixture, and the mixture was stirred for 10 minutes, followed by filtration. Subsequently, the thus-obtained crystals were reslurry-washed with n-hexane (50 mL), and then drying was carried out under reduced pressure (60° C., 12 hours), to thereby yield compound 8 as white powdery crystals (4.0 g, yield: 96.8%).

The thus-obtained compound 8 was subjected to NMR spectral analysis and IR spectral analysis. The results are shown below.

NMR (DMSO-$d_6$): 1.83 (qn, 2H, J=7 Hz), 2.45 (t, 2H, J=7 Hz), 2.78 (s, 6H), 3.39 (dd, 2H, J=5.5 Hz), 4.39 (dd, 2H, J=5.5 Hz) ppm IR (ATR): 2962, 2575, 2458, 1728 $cm^{-1}$ 9) Synthesis of 2-Dimethylamino-N-(2-{2-[2-(2-Dimethylamino-Acetylamino)-Ethoxy]-Ethoxy}-Ethyl)-Acetamide (Hereinafter May be Referred to as "Compound 9")

Compound 9 represented by the following formula (XIII):

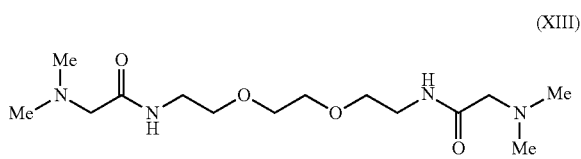 [SMILES: CN(C)CC(=O)NCCOCCOCCNC(=O)CN(C)C]

was synthesized as follows.

2,2'-(Ethylenedioxy)bisethylamine (2.0 g, 13.5 mmol) and N,N-dimethylglycine methyl ester (3.2 g, 26.0 mmol) were added to a 50-mL three-necked flask, and the mixture was stirred under a stream of nitrogen at 110 to 120° C. for 12 hours. Then, reaction was completed, to thereby yield an oily reaction mixture (4.3 g).

The thus-obtained oily reaction mixture was subjected to silica gel column chromatography (silica gel 60, 150 g), and elution was carried out with a solvent mixture of chloroform and methanol (chloroform:methanol=50:1 to 3:1), followed by concentration, to thereby yield compound 9 as pale yellow powdery crystals (2.3 g, yield: 54.5%).

The thus-obtained compound 9 was subjected to NMR spectral analysis and IR spectral analysis. The results are shown below.

NMR (DMSO-$d_6$): 2.19 (s, 12H), 2.84 (s, 4H), 3.25 (q, 4H, J=6 Hz), 3.43 (t, 4H, J=6 Hz), 3.50 (s, 4H), 7.68 (t, 4H, J=6 Hz) ppm IR (ATR): 3287, 2944, 2817, 2769, 1655, 1140 $cm^{-1}$ 10) Synthesis of 2-Dimethylamino-N-[8-(2-Dimethylamino-Acetylamino)-Octyl]-Acetamide (Hereinafter May be Referred to as "Compound 10")

Compound 10 represented by the following formula (XIV):

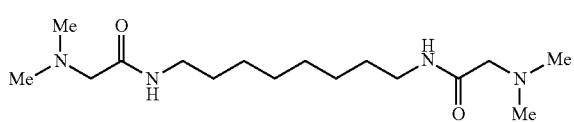

was synthesized as follows.

1,8-Diaminooctane (29.4 g, 0.20 mol) and N,N-dimethylglycine methyl ester (71.6 g, 0.60 mol) were added to a stainless steel (SUS316) simple autoclave (200 mL), followed by hermetic sealing. The autoclave was heated in an oil bath at 120 to 125° C. for seven hours.

After heating, the autoclave was left to cool to room temperature, and the resultant mixture was dissolved in a mixed solvent of ethanol (60.0 g) and ethyl acetate (150.0 g). Thereafter, the solution was washed twice with 5% aqueous sodium hydrogencarbonate solution (150 mL). The solution was concentrated under reduced pressure, and then the residue was recrystallized from a solvent mixture of acetone and hexane, followed by drying under reduced pressure at 50° C. for 12 hours, to thereby yield compound 10 as white powdery crystals (40.3 g, yield: 62.0%).

The thus-obtained compound 10 was subjected to NMR spectral analysis and IR spectral analysis. The results are shown below.

NMR (DMSO-$d_6$) δ: 1.12-1.30 (m, 8H), 1.37 (qn, 4H, J=6 Hz), 2.16 (s, 12H), 2.79 (s, 4H), 3.03 (q, 4H, H=6 Hz), 7.68 (t, 2H, 6 Hz) ppm IR (ATR): 3301, 2853, 2824, 2773, 1655 $cm^{-1}$ 11) Synthesis of 2-Dimethylamino-N-[2-(2-{2-[2-(2-Dimethylamino-Acetylamino)-Ethoxy]-Ethoxy}-Ethoxy)-Ethyl]-Acetamide (Hereinafter May be Referred to as "Compound 11")

Compound 11 represented by the following formula (XV):

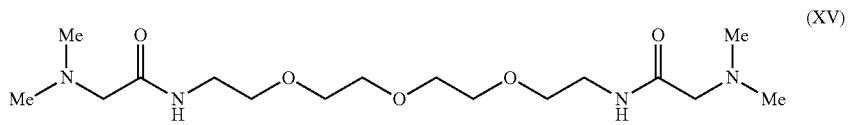 [SMILES: CN(C)CC(=O)NCCOCCOCCOCCNC(=O)CN(C)C]

was synthesized as follows.

Bis(3-aminoethyl)ether-diethylene glycol (5.0 g, 0.02 mol) was mixed with N,N-dimethylglycine methyl ester (8.0 g, 0.6 mol), and the mixture was stirred under a stream of nitrogen at 110 to 130° C. for 18 hours. Then, reaction was completed.

Subsequently, the resultant mixture was added to and dissolved in ethyl acetate (300 mL), and the solution was washed twice with 5% aqueous sodium hydrogencarbonate solution (50 mL). After concentration under reduced pressure, the resultant residue was subjected to silica gel column chromatography, and elution was carried out with a solvent mixture of chloroform and methanol. Thereafter, solvent was removed through evaporation, to thereby yield compound 11 as a pale yellow oily product (8.1 g, yield: 91.0%).

The thus-obtained compound 11 was subjected to NMR spectral analysis and IR spectral analysis. The results are shown below.

NMR (DMSO-$d_6$) δ: 1.64 (qn, 4H, J=6 Hz), 2.17 (s, 12H), 2.80 (s, 4H), 3.05 (q, 4H, J=6 Hz), 7.70 (t, 2H, J=6 Hz) ppm IR (ATR): 3323, 2863, 2824, 2777, 1660, 1098 $cm^{-1}$ 12) Synthesis of 2-Dimethylamino-N-[12-(2-Dimethylamino-Acetylamino)-Dodecyl]-Acetamide (Hereinafter May be Referred to as "Compound 12")

Compound 12 represented by the following formula (XVI):

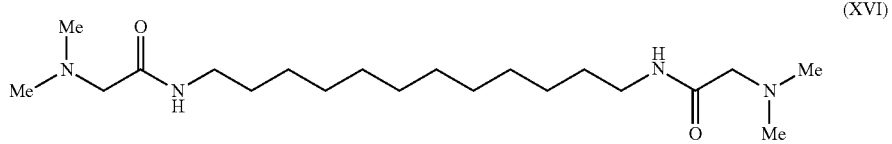 [SMILES: CN(C)CC(=O)NCCCCCCCCCCCCNC(=O)CN(C)C]

was synthesized as follows.

By using 1,12-diaminododecane (35.0 g, 0.18 mol) and N,N-dimethylglycine methyl ester (61.4 g, 0.53 mol), synthesis was carried out in a manner similar to that described above in the case of compound 10, to thereby yield compound 12 as white powdery crystals (49.4 g, yield: 91.7%).

The thus-obtained compound 12 was subjected to NMR spectral analysis and IR spectral analysis. The results are shown below.

NMR (DMSO-$d_6$) δ: 1.12-1.30 (m, 16H), 1.37 (qn, 4H, J=6 Hz), 2.16 (s, 12H), 2.80 (s, 4H), 3.04 (q, 4H, J=6 Hz), 7.69 (t, 2H, 6 Hz) ppm IR (ATR): 3288, 2850, 2816, 2763, 1655 $cm^{-1}$ 13) Synthesis of 2-Dimethylamino-N-[4-(2-Dimethylamino-Acetamino)-Butyl]-Acetamide (Hereinafter May be Referred to as "Compound 13")

Compound 13 represented by the following formula (XVII):

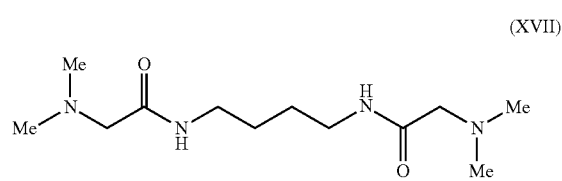 [SMILES: CN(C)CC(=O)NCCCCNC(=O)CN(C)C]

was synthesized as follows.

By using 1,4-diaminobutane (1.0 g, 0.01 mol) and N,N-dimethylglycine methyl ester (4.0 g, 0.03 mol), synthesis was carried out in a manner similar to that described above in the case of compound 10, to thereby yield compound 13 as white powdery crystals (0.1 g, yield: 5.0%).

The thus-obtained compound 13 was subjected to NMR spectral analysis and IR spectral analysis. The results are shown below.

NMR (DMSO-$d_6$) δ: 1.37 (t, 4H, J=7 Hz), 2.18 (s, 12H), 2.81 (s, 4H), 3.14 (q, 4H, J=6 Hz), 3.41 (t, 4H, J=6 Hz), 3.46-3.56 (m, 8H), 7.74 (t, 2H, 6 Hz) ppm IR (ATR): 3288, 2847, 2820, 2773, 1650 $cm^{-1}$ Example 2

Evaluation of the Hair Growth Suppressing Effect of the Compound of the Present Invention by an Organ Culture Method Using Porcine Hair Follicles The skin of a pork pig was cut into pieces of appropriate size, and excess fat was removed. For disinfection, the skin pieces were immersed in a Hibitane solution under sterile conditions for 10 to 20 minutes. The thus-disinfected skin pieces were washed several times with D-PBS.

Subsequently, hair follicles were isolated from the thus-treated skin pieces under a stereomicroscope by means of tweezers and a scalpel (FEATHER No. 10), and the hair follicles were placed on William's Medium E (Gibco cat. No. 12551-032) supplemented with penicillin/streptomycin (Gibco cat. No. 15140-122) solution by 10.

The isolated hair follicles were transferred to a 24-well culture plate (one follicle/well) together with the aforementioned culture medium (400 µL), and cultured in an incubator (37° C., 5% $CO_2$) for two days. Hair follicle that exhibited an elongation more than 0.15 mm was employed for evaluation.

Subsequently, compounds synthesized in Example 1 (compounds 2, 6, 7, and 9 to 13) were diluted with the aforementioned culture medium, to thereby prepare sample-containing media. Each of the thus-prepared sample-containing media was used for replacement. Similarly, N,N-dimethylglycine methyl ester (DMG) and 1,8-diaminooctane (1,8-DAO) were diluted with the aforementioned culture medium, to thereby prepare sample-containing media. Each of the thus-prepared sample-containing media was also used for replacement.

The medium for culture of hair follicles was replaced with each of the sample-containing media, and thereafter, replaced with a sample-containing medium every one or two days. At days five or six after the start of culture with the sample-containing medium, the elongation of hair follicles (i.e., elongation of hair) was measured and compared with that of the control in which medium was replaced with only the non-sample-containing medium. The elongation of hair follicles (i.e., elongation of hair) in the control medium was taken as 100%.

The sample concentration of each sample-containing medium was set within a range that the sample is completely dissolved in the medium, and at non-cytotoxic levels which cause no reduction of cell viability with 24-hour addition of the sample to epidermal cells.

The results are shown in Tables 1 and 2. Table 1 shows percent growth of hair follicles determined six days after the start of culture with each of the sample-containing media. While Table 2 shows percent growth of hair follicles determined five days after the start of culture with each of the sample-containing media.

TABLE 1

Percent growth of hair follicles at day 6

| Sample | Concentration | Percent growth of hair follicles (control = 100%) |
|---|---|---|
| Compound 9 | 0.01% | 62.4% |
| Compound 10 | 0.01% | 54.7% |
| DMG | 0.03% | 91.8% |
| 1,8-DAO | 0.03% | 87.9% |

TABLE 2

Percent growth of hair follicles at day 5

| Sample | Concentration | Percent growth of hair follicles (control = 100%) |
|---|---|---|
| Compound 2 | 0.00003% | 108.5% |
| Compound 6 | 0.003% | 91.6% |

TABLE 2-continued

Percent growth of hair follicles at day 5

| Sample | Concentration | Percent growth of hair follicles (control = 100%) |
|---|---|---|
| Compound 7 | 0.00003% | 42.4% |
| Compound 11 | 0.003% | 97.0% |
| Compound 12 | 0.003% | 48.7% |
| Compound 13 | 0.003% | 79.1% |

As shown in Tables 1 and 2, compound 7 (0.000030) exhibited the highest suppressive effect on growth of hair follicles (i.e., hair growth), which was followed by compound 12 (0.003%), compound 10 (0.01%), compound 9 (0.01%), and compound 13 (0.003%).

What is claimed is:

1. A method for regulating hair growth, comprising administering, to a subject in need thereof, a compound represented by the following formula (I):

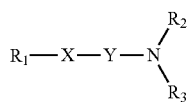

[wherein $R_1$ represents an unsubstituted, linear C2 alkyl group; or
a group represented by the following formula (II):

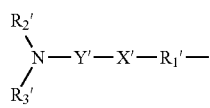

(wherein
$R_1'$ represents an unsubstituted, linear C4, C8 or C12 alkylene group, or —$(CH_2)_n$—{O—$(CH_2)_m$}$_o$—O—$(CH_2)_p$— in which each of n, m, o, and p is an integer and n=2, m=2, o=1 or 2, and p=2;
X' represents —CO—NH—;
Y' represents an unsubstituted C1 alkylene group;
$R_2'$ represents a C1 alkyl group; and
$R_3'$ represents a C1 alkyl group)
X represents —NH—CO—;
Y represents an unsubstituted C1 alkylene group;
$R_2$ represents a C1 alkyl group; and
$R_3$ represents a C1 alkyl group]
or a salt of the compound; and/or
a quaternary ammonium salt represented by the following formula (IV):

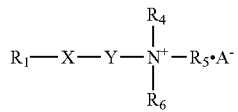

(wherein $R_1$, is an unsubstituted, linear C12 alkyl group, X is —NH—CO—, Y is an unsubstituted C1 alkylene and $R_4$, $R_5$, and $R_6$ each represent a C1 alkyl group and $A^-$ represents a chloride counter ion).

2. The method for regulating hair growth according to claim 1, which comprises administering, to a subject in need thereof, a compound selected from the group consisting of
2-dimethylamino-N-ethyl-acetamide,
dodecylcarbamoylmethyltrimethylammonium chloride,
2-dimethylamino-N-(2-{2-[2-(2-dimethylamino-acetylamino)-ethoxy]-ethoxy}-ethyl)-acetamide,
2-dimethylamino-N-[8-(2-dimethylamino-acetylamino)-octyl]-acetamide,
2-dimethylamino-N-[2-(2-{2-[2-(2-dimethylamino-acetylamino)-ethoxy]-ethoxy}-ethoxy)-ethyl]-acetamide,
2-dimethylamino-N-[12-(2-dimethylamino-acetylamino)-dodecyl]-acetamide, and
2-dimethylamino-N-[4-(2-dimethylamino-acetamino)-butyl]-acetamide.

3. The method for regulating hair growth according to claim 1, wherein said compound is said 2-dimethylamino-N-ethyl-acetamide.

4. The method for regulating hair growth according to claim 1, wherein said compound is said dodecylcarbamoylmethyltrimethylammonium chloride.

5. The method for regulating hair growth according to claim 1, wherein said compound is said 2-dimethylamino-N-(2-{2-[2-(2-dimethylamino-acetylamino)-ethoxy]-ethoxy}-ethyl)-acetamide.

6. The method for regulating hair growth according to claim 1, wherein said compound is said 2-dimethylamino-N-[8-(2-dimethylamino-acetylamino)-octyl]-acetamide.

7. The method for regulating hair growth according to claim 1, wherein said compound is said 2-dimethylamino-N-[2-(2-{2-[2-(2-dimethylamino-acetylamino)-ethoxy]-ethoxy}-ethoxy)-ethyl]-acetamide.

8. The method for regulating hair growth according to claim 1, wherein said compound is said 2-dimethylamino-N-[12-(2-dimethylamino-acetylamino)-dodecyl]-acetamide.

9. The method for regulating hair growth according to claim 1, wherein said compound is said 2-dimethylamino-N-[4-(2-dimethylamino-acetamino)-butyl]-acetamide.

* * * * *